(12) United States Patent
Mrzena et al.

(10) Patent No.: US 9,540,597 B2
(45) Date of Patent: *Jan. 10, 2017

(54) PROCESS FOR THE PREPARATION OF A POWDER COMPRISING ONE OR MORE COMPLEXING AGENT SALTS

(75) Inventors: Frank Mrzena, Mutterstadt (DE); Ullrich Menge, Grenzach-Wyhlen (DE); Michael Schoenherr, Frankenthal (DE); Thomas Heidenfelder, Hirschberg (DE)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/501,390

(22) PCT Filed: Oct. 11, 2010

(86) PCT No.: PCT/EP2010/065184
§ 371 (c)(1),
(2), (4) Date: Apr. 11, 2012

(87) PCT Pub. No.: WO2011/045266
PCT Pub. Date: Apr. 21, 2011

(65) Prior Publication Data
US 2012/0202731 A1 Aug. 9, 2012

(30) Foreign Application Priority Data

Oct. 12, 2009 (EP) .................................. 09172810

(51) Int. Cl.
| C11D 11/02 | (2006.01) |
| C11D 3/33 | (2006.01) |
| C11D 17/06 | (2006.01) |
| C07C 227/42 | (2006.01) |
| C07C 229/24 | (2006.01) |
| C11D 11/00 | (2006.01) |

(52) U.S. Cl.
CPC .............. *C11D 3/33* (2013.01); *C07C 227/42* (2013.01); *C07C 229/24* (2013.01); *C11D 11/0088* (2013.01); *C11D 11/02* (2013.01); *C11D 17/06* (2013.01)

(58) Field of Classification Search
CPC ...... C07C 227/42; C07C 229/24; C11D 11/02; C11D 11/0082; C11D 11/0088; C11D 17/06; C11D 3/33
USPC .............................. 510/443, 452, 480; 264/12
See application file for complete search history.

(56) References Cited

U.S. PATENT DOCUMENTS

| 2,728,678 | A | 12/1955 | Sharp et al. |
| 2,970,057 | A | 1/1961 | Terrett et al. |
| 3,615,723 | A | 10/1971 | Meade |
| 3,629,955 | A * | 12/1971 | Davis et al. .................... 34/174 |
| 3,717,589 | A * | 2/1973 | Feiler et al. ................... 510/533 |
| 3,735,792 | A | 5/1973 | Asizawa et al. |
| 3,950,275 | A * | 4/1976 | Toyoda et al. ................ 510/441 |
| 3,956,379 | A * | 5/1976 | Beaver .......................... 562/554 |
| 4,070,766 | A | 1/1978 | Kamphuis |
| 4,698,174 | A * | 10/1987 | Denzinger et al. ........... 510/533 |
| 5,100,509 | A | 3/1992 | Pisecky et al. |
| 5,786,313 | A | 7/1998 | Schneider et al. |
| 5,849,950 | A | 12/1998 | Greindl et al. |
| 5,945,032 | A * | 8/1999 | Breitenbach et al. ... 252/186.29 |
| 5,968,884 | A | 10/1999 | Gopalkrishnan et al. |
| 5,981,798 | A | 11/1999 | Schoenherr et al. |
| 6,451,224 | B1 * | 9/2002 | Wilson ..................... 252/182.29 |
| 6,815,410 | B2 * | 11/2004 | Boutique et al. ............. 510/295 |
| 6,845,571 | B1 | 1/2005 | Schwarz et al. |
| 6,906,215 | B1 * | 6/2005 | Tanaka et al. ................ 556/148 |

(Continued)

FOREIGN PATENT DOCUMENTS

| CN | 102574083 A | 7/2012 |
| DE | 1 261 619 | 2/1968 |

(Continued)

OTHER PUBLICATIONS

International Preliminary Report on Patentability Issued Dec. 23, 2011 in PCT/EP10/65184 Filed Oct. 11, 2010.

(Continued)

*Primary Examiner* — Lorna Douyon
(74) *Attorney, Agent, or Firm* — Oblon, McClelland, Maier & Neustadt, L.L.P.

(57) ABSTRACT

A process for the preparation of a powder comprising one or more complexing agent salts of the general formula

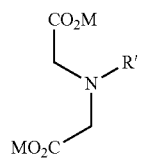

comprises atomizing an aqueous solution comprising the one or more complexing agent salts in the presence of a crystalline fine dust of the same complexing agent salts and a drying step, wherein the concentration of the one or more complexing agent salt is from 10 to 80% by weight, based on the total weight of the aqueous solution, with an upper limit for the average particle diameter of the crystalline fine dust which is lower by at least a factor of 2 than the lower limit of the average particle diameter of the powder obtained after the process, and the fraction of the crystalline fine dust is from 0.1 to 20% by weight, based on the weight of the powder obtained after the process.

15 Claims, 2 Drawing Sheets

(56) References Cited

U.S. PATENT DOCUMENTS

| | | | |
|---|---|---|---|
| 7,442,679 B2* | 10/2008 | Stolte et al. | 510/445 |
| 7,671,234 B2 | 3/2010 | Oftring et al. | |
| 8,754,026 B2* | 6/2014 | Blei et al. | 510/457 |
| 8,940,678 B2* | 1/2015 | Baranyai | 510/349 |
| 2002/0046427 A1 | 4/2002 | Nambu et al. | |
| 2003/0114717 A1 | 6/2003 | Erdmann et al. | |
| 2010/0056817 A1* | 3/2010 | Meunier et al. | 556/112 |
| 2010/0167975 A1 | 7/2010 | Vandermeulen et al. | |
| 2012/0071381 A1 | 3/2012 | Mrzena et al. | |
| 2012/0077727 A1* | 3/2012 | Blei et al. | 510/480 |

FOREIGN PATENT DOCUMENTS

| | | |
|---|---|---|
| DE | 1261619 | 2/1968 |
| DE | 2 125 945 | 12/1971 |
| DE | 2125945 | 12/1971 |
| EP | 0 845 456 | 6/1998 |
| JP | 3-65233 A | 3/1991 |
| JP | 2003-501252 A | 1/2003 |
| JP | 2004-2290 A | 1/2004 |
| JP | 2004-175930 A | 6/2004 |
| RU | 2250131 | 4/2005 |
| WO | 94 29421 | 12/1994 |
| WO | 2006 120129 | 11/2006 |
| WO | 2009 092699 | 7/2009 |
| WO | WO 2009-092699 | 7/2009 |
| WO | 2009 103822 | 8/2009 |
| WO | WO 2009-103822 | 8/2009 |
| WO | WO 2011/023382 A2 | 3/2011 |

OTHER PUBLICATIONS

U.S. Appl. No. 13/430,105, filed Mar. 26, 2012, Baumann, et al.
International Search Report Issued Feb. 8, 2011 in PCT/EP10/65184 Filed Oct. 11, 2010.
U.S. Appl. No. 61/253,911, filed Oct. 22, 2009, Mrzena, et al.
Office Action in Russian counterpart patent application No. 2012 119 166, dated Feb. 12, 2015.
Brochure "Trilon M types", TI/EVD 1418e, BASF The Chemical Company, May 2007, 14 pages.
Peter Bork, "Spray Drying Plants for Manufacture of Dustless Powders—A Technical Note", Technical Note, JTTEE5 10:, vol. 10(4), Dec. 2001, pp. 578-583.

* cited by examiner

PROCESS FOR THE PREPARATION OF A POWDER COMPRISING ONE OR MORE COMPLEXING AGENT SALTS

FIELD OF THE INVENTION

The invention relates to a process for the preparation of a powder comprising one or more complexing agent salts of the general formula I

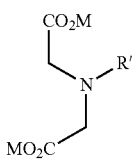

(I)

and to a use of the above powders.

BACKGROUND OF THE INVENTION

The aminopolyphosphonates, polycarboxylates or aminopolycarboxylates, such as ethylenediaminetetraacetic acid (EDTA), often used as complexing agents for example in detergents and cleaners are biodegradable only to a small degree.

A cost-effective alternative is the glycine-N,N-diacetic acid derivatives, such as methylglycine-N,N-diacetic acid (MGDA) and salts thereof—e.g. the trialkali metal salts—which have advantageous toxicological properties and are readily biodegradable. The use of MGDA and of related glycine-N,N-diacetic acid derivatives in cleaners, and the syntheses thereof are described e.g. in WO-A 94/029421 or U.S. Pat. No. 5,849,950. For a cost-effective production of the glycine-N,N-diacetic acid derivatives, high requirements are placed on the yield of the individual synthesis steps and purity of the isolated intermediate products.

MGDA is prepared in particular by reacting iminodiacetonitrile with acetaldehyde and hydrocyanic acid or of alpha-alanine nitrile with formaldehyde and hydrocyanic acid and alkaline hydrolysis of the methylglycinediacetonitrile (MGDN) obtained as intermediate product with sodium hydroxide solution, giving the trisodium salt of MGDA. In order to achieve high MGDA yields and purities, MGDN is generally isolated as an intermediate product and used as pure substance in the subsequent hydrolysis step.

A problem with the hydrolysis of alkylglycinenitrile-N,N-diacetonitriles is their thermal lability, especially in an alkaline medium. As a result of the sterically demanding alkyl substitution, back-cleavage reactions are favored. Consequently, processes have been developed which as far as possible lead to low by-product forms of MGDA and its salts.

An improved process for the preparation of low by-product salts of MGDA is described in WO 2006/120129. The more modern production processes generally lead to about 35-40% strength by weight aqueous solutions, from which the salts are then prepared in flowable form.

One of the known work-up processes in the prior art is the conversion of such aqueous solutions in a spray-tower. This produces predominantly amorphous powders with a residual moisture in the order of magnitude of for example 5% by weight. Although higher residual moistures are conceivable, they are rather difficult to generate in a spray-tower and are, moreover, also undesired because then upon subsequent storage by the consumer or during processing, clumping of the powders can arise. It is also known that granules do not have such disadvantages and can therefore be processed without problems. However, granule production requires an additional reworking step following powder production in the spray-tower and is therefore relatively expensive. In this reworking step, additional moisture is fed to the powder from the spray-tower, and granulation is carried out with heating and kneading at a residence time in the order of magnitude of one hour via a crystallization. Such a process is described for example in EP-A 08 45 456.

SUMMARY OF THE INVENTION

Accordingly, it was an object of the invention to provide a technically simple process for the preparation of powders of the above complexing agent salts which have the properties desired for the further use thereof, in particular good storage and processing properties, which have an increased degree of crystallinity and an increased residual moisture in the range from about 7 to 14% by weight, based on the total weight of the powder, and are granule-like.

The object is achieved by a process for the preparation of a powder comprising one or more complexing agent salts of the general formula

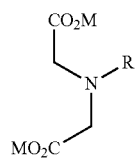

(I)

in which
R' is hydrogen or one of the groups

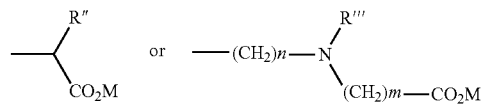

where
R" is hydrogen, a $C_1$-$C_{12}$-alkyl radical or a —$(CH_2)_q$—COOM radical where q=1 to 5
n and m are in each case an integer from 0 to 5 and
R''' is hydrogen or a $C_1$-$C_{12}$-alkyl radical or a $C_2$-$C_{12}$-alkenyl radical which may be additionally substituted by up to 5 hydroxyl groups, or one of the groups

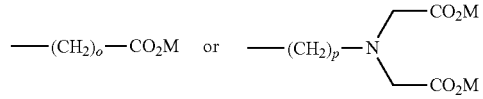

in which o and p are in each case an integer from 0 to 5, and
M, independently of the others, is hydrogen, alkali metal, alkaline earth metal, ammonium or substituted ammonium in the corresponding stoichiometric amounts,
starting from an aqueous solution comprising the one or more complexing agent salts in a concentration of from 10 to 80% by weight, based on the total weight of the aqueous solution, in a spray-drying process, comprising an atomization step and a drying step, wherein the atomization step is carried out with the addition of crystalline fine dust of the same complexing agent salt(s) as are present in the aqueous solution, or one or more complexing agent salts different therefrom of the above formula I, with an upper limit for the average particle diameter of the crystalline fine dust which is lower by at least a factor of 2 than the lower limit of the average particle diameter of the powder obtained after the process, in a fraction of from 0.1 to 20% by weight, based on the weight of the powder obtained after the process.

It has been found that it is possible to obtain, in a simple spray-drying process, powders of the above complexing agent salts which have the properties desired for storage and processing by starting from an aqueous solution of the same which is atomized in the presence of a crystalline fine dust which has significantly smaller particle dimensions than the lower limit of the average particle diameter of the powder obtained after the process.

DETAILED DESCRIPTION OF THE INVENTION

It is essential to the process according to the invention that in the atomization step a spray is provided which comprises, in a continuous phase of an inert gas, in particular air, as disperse phase, liquid droplets of the aqueous starting solution comprising the one or more complexing agent salts and in addition a further disperse solid phase comprising the crystalline fine dust of one or more complexing agent salts. It is assumed that the crystalline fine dust offers crystallization seeds during the drying process, on which the droplets of the aqueous solution can crystallize out and grow. Moreover, by returning the fine, dried spray powder to the drying zone, the particle size in the same can be increased and the granulometry of the powder obtained in the process can be influenced in a positive manner. Moreover, the crystalline fine powder also has the effect of powdering the wet powder obtained in the spray-drying plant.

Within the context of the present invention, the term powder is understood as meaning a flowable solid which has average particle sizes in the range from ca. 1 μm to ca. 10 mm; for the coarser particles from the range defined above, above ca. 100 μm, the term "granules" can also be used as an alternative.

The powder comprising one or more of the above complexing agent salts is prepared according to the invention in a spray-drying process.

The historically evolved subject-specific terms in the field of spray-drying are often not used uniformly; consequently, the terms relevant for the present invention will be explained below:

The term spray-drying process refers in the present case as a generic term to all processes in which a liquid starting material, which may be present as solution or dispersion, is atomized and dried with the aim of producing a solid. A spray-drying process is characterized by the process steps of atomization and drying. These can be carried out in the same apparatus or else in successively connected regions of the same apparatus.

The first process step of any spray-drying process is the atomization of the liquid starting material into an inert gas, generally air, giving a spray, the spray comprising, as continuous phase, the inert gas, generally air, and, as disperse continuous phases, finely distributed liquid droplets of the liquid starting material and, moreover, additionally, depending on the process of the invention, a disperse solid phase formed from the crystalline fine dust of the one or more complexing agent salts. The spray is characterized by a certain droplet size distribution and droplet size distribution width (span).

To the generic term spray-drying process are subsumed in particular the specific processes listed below:

Spray-drying in the narrower sense, agglomerating spray-drying, spray-agglomeration and spray-granulation.

Spray-drying in the narrower sense is the historically oldest spray-drying process. It is carried out in spray-towers. The first spray-towers were built in the 1930s by Niro. Although the structures of spray-towers are different, the principle remains the same: from each droplet of the spray obtained in the spray-tower, in each case precisely one particle should be formed. Since the residence time in the spray-towers is limited, the droplets in the spray-tower must only be very small in order to be able to dry in the spray-tower. The average particle size of spray powders which is obtained by spray-drying in the narrower sense is often in the range from ca. 50 μm to about 300 μm.

According to a preferred embodiment of spray-drying in spray-towers, a so-called agglomerating spray-drying can be carried out, which was developed by spray-tower manufacturers in the 1980s in order to reduce the dust fraction in the spray powder. In this process, the fines fraction of the spray powder is separated in the spray-tower and recycled into the region of the atomizer. There, the particles come into contact with the still-liquid spray and are able to agglomerate, i.e. two or more small particles join together to give in each case a larger particle, the so-called agglomerate. Since the agglomerates require longer drying times compared with individual particles, a fluidized bed is integrated into the spray-tower for the purpose of increasing the residence time. Spray-towers of this type with integrated fluidized bed are known for example as Fluidized Spray Dryer (FSD) from Niro or Spray Bed Dryer (SBD) from Anhydro.

In a further variant of a spray-drying process, so-called spray-agglomeration, powder, which is present in a mixer with agitated internals, is bound by spraying in binding fluid to give larger particles, so-called agglomerates. In the case of spray-agglomeration in a mixer, a dryer must be connected downstream, which may be in particular a fluidized bed. The spray-agglomeration can either be carried out continuously or discontinuously.

In a further process variant of the spray-drying process, so-called spray-granulation, the liquid starting material is sprayed into a fluidized bed. The drops of the spray are deposited here predominantly on the granules already present in the fluidized bed and contribute to their further growth. The end product is often obtained by sieving or screening from the broader fluidized-bed fraction. Coarse material is often ground and returned to the fluidized bed together with the separated-off fines materials. The process is therefore more complicated than spray-drying in the narrower sense or spray-agglomeration. However, it is possible to achieve larger particles and narrower particle size distributions.

The spray-drying process according to the invention can preferably be carried out in each of the process variants described above, it being obligatory in each case that in the atomization step crystalline fine dust of the same complexing agent salt(s) as are present in the aqueous starting solution, or one or more complexing agent salts of the above formula I different therefrom are used, with an upper limit for the average particle diameter of the crystalline fine dust which is lower by at least a factor of 2 than the lower limit of the average particle diameter of the powder obtained after the spray-drying process.

The average particle diameters of the crystalline fine dust and of the powder obtained after the process according to the invention are usually determined by methods such as laser diffraction (e.g. Malvern) or optical methods (e.g. CamSizer).

If the spray-drying process carried out is spray-drying in the narrower sense, the average particle diameters of the powders obtained afterwards are often in a range from ca. 50 to 300 μm. Accordingly, in the atomization step, crystalline fine dust with an upper limit for the average particle diameter of at most 25 μm must be used.

BRIEF DESCRIPTION OF THE DRAWINGS

A more complete appreciation of the disclosure and many of the attendant features thereof will be readily obtained as the same becomes better understood by reference to the following detailed description when considered in connection with the accompanying drawings, wherein.

Figure 1:
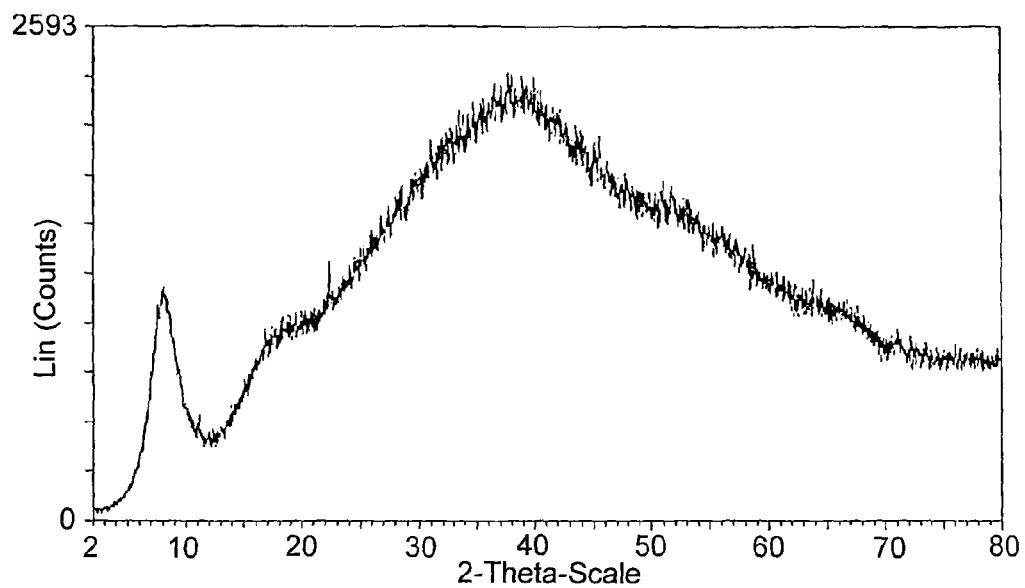
FIG. 1 shows an X-ray diffractogram for the powder obtained according to working example 1 (for comparison).

If the spray-drying process carried out is a spray-granulation, then powders are obtained which often have an average particle diameter in the range from about 200 to 2000 μm. Accordingly, it is necessary to use crystalline fine dust for which the permissible upper limit for the average particle diameter is at most 100 μm.

According to the invention, the weight fraction for the addition of crystalline fine dust in the spray-drying process is in the range from about 0.1 to 20% by weight, based on the weight of the powder obtained after the process, preferably about 4 to 10% by weight, based on the total weight of the powder obtained after the process.

Preferably, the starting material used is an aqueous solution which is obtained by the corresponding synthesis and which comprises ca. 30 to 50% by weight of the one or more complexing agent salts, and which is concentrated in a process step connected upstream of the spray-drying process in a heat exchanger or a thin-film evaporator to ca. 55 to 80% by weight of complexing agent salts, based on the total weight of the aqueous solution.

The one or more complexing agent salts correspond to the general formula

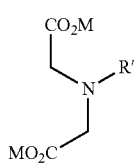
(I)

in which
R' is hydrogen or one of the groups

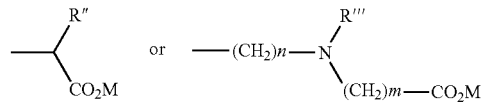

where
R" is hydrogen, a $C_1$-$C_{12}$-alkyl radical or a —$(CH_2)_q$—COOM radical where q=1 to 5
n and m are in each case an integer from 0 to 5 and
R''' is hydrogen or a $C_1$-$C_{12}$-alkyl radical or a $C_2$-$C_{12}$-alkenyl radical which may be additionally substituted by up to 5 hydroxyl groups, or one of the groups

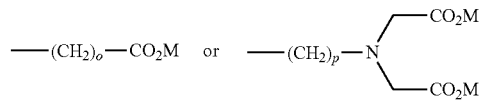

in which o and p are in each case an integer from 0 to 5, and
M, independently of the others, is hydrogen, alkali metal, alkaline earth metal, ammonium or substituted ammonium in the corresponding stoichiometric amounts.

These are preferably derivatives of glycine-N,N-diacetic acid or derivatives of glutamine-N,N-diacetic acid. Preference is also given to derivatives of ethylenediaminetriacetic acid or of nitrilotriacetic acid.

Particularly preferred derivatives of glycine-N,N-diacetic acid are alkali metal salts of methylglycine-N,N-diacetic acid, referred to below as MGDA.

The drying step of the spray-drying process is preferably carried out at a pressure in the range from about 0.1 bar absolute to 10 bar absolute, in particular at a pressure in the range from about 0.8 bar absolute to 2 bar absolute.

The residence time in the drying step is preferably in a range from about 10 seconds up to 1 h.

The invention also provides a formulation comprising the powder obtained according to the process described above, or an aqueous solution of the same, as complexing agent for alkaline earth metal ions and heavy metal ions in the amounts customary for this, besides other customary constituents of such formulations.

The formulations may in particular be detergents and cleaner formulations.

The invention also further provides the use of a powder obtained by the above process for producing compression agglomerates, and also the use of the compression agglomerates for use in solid cleaners.

The above cleaners may in particular be intended for automatic dishwashers. In particular, these may be tablets for dishwashers.

The spray-drying process according to the invention can also be carried out with mixtures of one or more complexing agent salts and further substances. Further substances are to be understood in particular as meaning auxiliaries and additives customarily used in the detergents and cleaners industry. For example, surfactants, polymers, inorganic salts, and/or citrates can be used. For use in the field of machine dishwashing, for example inorganic salts, such as carbonates, sulfates, phosphates, silicates; organic salts such as citrates; polymers, such as polycarboxylates or sulfonated polymers or phosphonates are suitable. As a result of mixtures of this type, the production process for producing detergents and cleaners can be designed more simply.

The powders obtained by the above process can in particular also be used in mixtures with customary auxiliaries and additives.

According to the process of the invention, it is possible in particular to obtain a methylglycine-N,N-diacetic acid trisodium salt powder with a degree of crystallinity of ≥30% comprising a first crystalline modification with the d values stated below in Angstroms at the diffraction angles 2-theta in °:

| 2-theta (°) | d value (Angströms) |
|---|---|
| 8.4 | 10.5 |
| 9.5 | 9.3 |
| 11.1 | 8.0 |
| 13.2 | 6.7 |
| 13.9 | 6.35 |
| 15.8 | 5.6 |
| 16.5 | 5.36 |
| 16.84 | 5.26 |
| 17.34 | 5.11 |
| 17.67 | 5.02 |
| 18.92 | 4.69 |
| 20.29 | 4.37 |
| 21.71 | 4.09 |
| 22.3 | 3.98 |
| 23.09 | 3.85 |
| 24.74 | 3.59 |
| 25.36 | 3.51 |
| 27.04 | 3.29 |
| 28.28 | 3.15 |
| 29.63 | 3.01 |
| 30.09 | 2.97 | and/or a second crystalline modification with the d values in Angströms at the respective diffraction angles 2-theta in ° in the X-ray powder diffractogram corresponding to the table below:

| 2-theta (°) | d value (Angströms) |
|---|---|
| 8.2 | 10.80 |
| 10.5 | 8.40 |
| 15.55 | 5.70 |
| 16.47 | 5.38 |
| 17.09 | 5.18 |
| 18.10 | 4.90 |
| 18.82 | 4.71 |
| 21.00 | 4.23 |
| 21.35 | 4.16 |
| 22.64 | 3.92 |
| 23.69 | 3.75 |
| 24.73 | 3.60 |
| 26.75 | 3.33 |
| 28.93 | 3.08 |
| 29.88 | 2.99 |
| 31.46 | 2.84 |
| 31.88 | 2.80 |

The invention is illustrated in more detail below by reference to a drawing and working examples.

Figure 2:
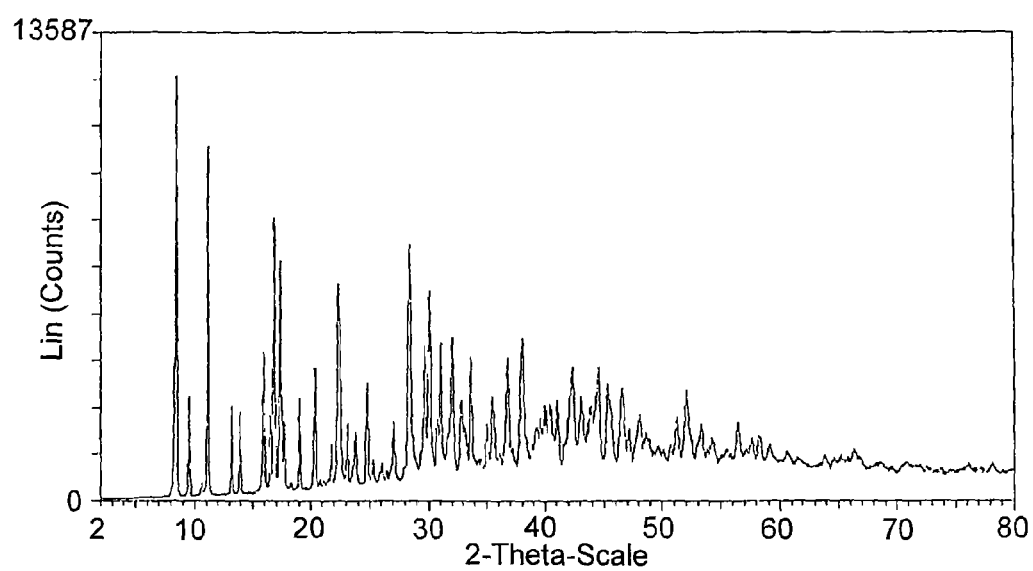
FIG. 2 shows X-ray diffractograms for powders obtained in Example 2.
Figure 3:
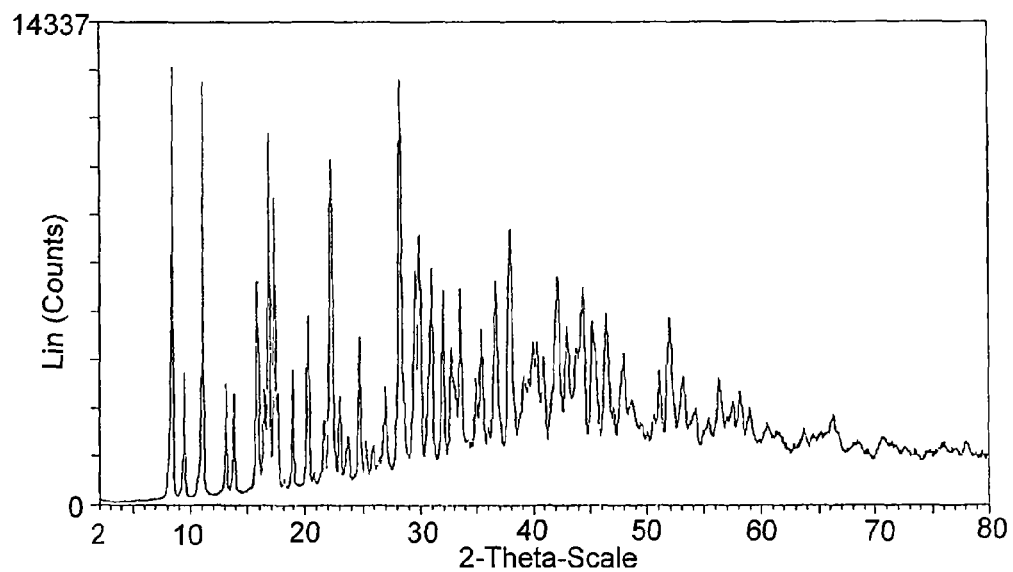
FIG. 3 shows X-ray diffractograms for powders obtained in Example 3.
Figure 4:
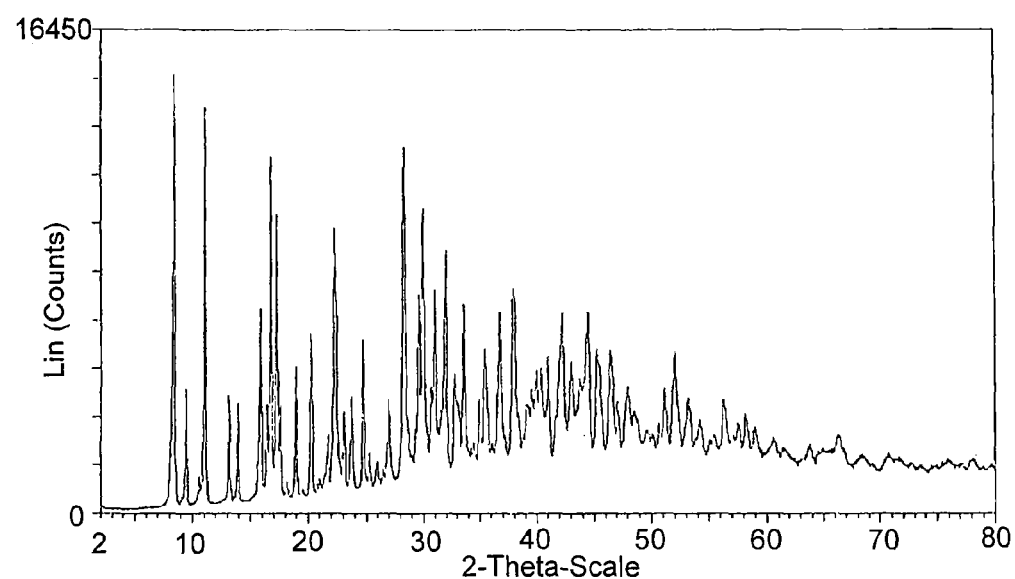
FIG. 4 shows X-ray diffractograms for powders obtained in Example 4.

In the drawing specifically:

FIG. 1 shows an X-ray diffractogram for the powder obtained according to working example 1 (for comparison), FIGS. 2 to 4 show X-ray diffractograms for powders obtained in each case according to working examples 2 to 4 (according to the invention).

Here, in the figures, the abscissa shows the diffraction angle 2-theta in °, and the ordinate shows the measured intensity, in counts (pulses) (dimensionless).

The X-ray powder diffractometer measurements were carried out on a D8 Advance® diffractometer from Bruker AXS (Karlsruhe). In reflection with Cu—K α-radiation was measured with a variable diaphragm adjustment on the primary side and on the secondary side. The measurement range was 2° to 80° 2-theta, the step width 0.01° and the measurement time per angle step 3.6 seconds.

The degree of crystallinity was ascertained from the X-ray powder diffractograms in a known manner by, as usual, determining the surface fraction of the crystalline phase and of the amorphous phase and using these to calculate the degree of crystallinity, CD, as the ratio of the area of the crystalline phase, $I_c$, to the total area, consisting of the area of the amorphous phase, $I_a$, and the area of the crystalline phase, $I_c$:

$$CD=I_c/(I_c+I_a).$$

The determination of the degree of crystallinity can be carried out in particular using a software program, for example the software program TOPAS® from Bruker AXS.

For this, firstly an amorphous sample is measured and the linear course is fitted in a profile fit with the help of six individual lines. The line positions of these lines and their half-widths are then fixed and these values are saved as "amorphous phase".

For the sample to be measured for which the degree of crystallinity is to be determined, the surface fraction of the crystalline phase and the surface fraction of the amorphous phase is then determined and the degree of crystallinity CD is calculated therefrom in accordance with the formula given above.

The amorphous phase is used as defined above.

The crystalline phase can likewise be defined via its individual line positions analogously to the amorphous phase, or by reference to the following lattice constants, as so-called (hkl) phase (a=33.63, b=11.36 and c=6.20 and space group Pbcm), where the lattice parameters are variables which can be freely refined. The background is fitted as polynomial of the 1st degree.

The program TOPAS® calculates the optimal fit between measured diffractogram and the theoretical diffractogram consisting of amorphous and crystalline phase.

WORKING EXAMPLES

Working Example 1 (for Comparison)

Classic Spray-Drying without the Addition of Crystalline Fine Dust

A quantitative stream of 60 kg/h of an aqueous solution of Na3-MGDA with a solids content of 40% was evaporated in a plate heat exchanger evaporator (heating area 1.7 m²) to a solids content of 59% and separated in a separating container. The evaporation was carried out at a wall temperature of 152° C. (steam heating) and at a pressure of 2.5 bar abs in the separator.

The evaporated solution was metered into the downstream piston membrane pump at a temperature of ca. 128° C. using a gear pump and sprayed into a spray-tower using a single-material nozzle.

The spray-tower had a diameter of 800 mm and a length of 12 m. The spray-tower was operated with a quantity of air of 1400 kg/h and a gas inlet temperature of 160° C. The product outlet temperature was 127° C. and the solids content of the dry product 94.1%. The product was separated out via a 2-point discharge (directly at the spray-tower and at the downstream filter).

The product prepared in this way was a pourable powder. The bulk density was 529 kg/m$^3$. X-ray structural analysis shows that the product is amorphous.

The storage behavior of this sample was evaluated in a desiccator test. For this, a 3 g sample is stored in an open weighing cup in a desiccator at 20° C. and a relative atmospheric humidity of 76% over a period of 144 hours. The mass increase of the sample is then ascertained and the pourability of the sample is evaluated. The mass increase was 27.1% and the sample had started to dissolve, i.e. it was wet and no longer pourable.

Working Example 2 (According to the Invention)

Spray-Tower with the Addition of Crystalline Fine Dust

A quantitative stream of 75 kg/h of an aqueous solution of Na3-MGDA with a solids content of 40% was evaporated in a plate heat exchanger evaporator (heating area 1.7 m$^2$) to a solids content of 60% and separated in a separating container. The evaporation was carried out at a wall temperature of 156° C. (steam heating) and at a pressure of 2.5 bar abs in the separator.

The evaporated solution was metered into the downstream piston membrane pump at a temperature of ca. 130° C. using a gear pump and sprayed into a spray-tower using a single-material nozzle.

The spray-tower had a diameter of 800 mm and a length of 12 m. The spray-tower was operated with a quantity of air of 1400 kg/h and a gas inlet temperature of 202° C. A mass stream of 4 kg/h of crystalline fine dust Na3-MGDA was blown into the spray-tower by means of an injector. The product outlet temperature was 99° C. and the solids content of the dry product 90.2%. The product was separated out via a 2-point discharge (directly at the spray-tower and at the downstream filter).

The product prepared in this way was a pourable powder. The bulk density was 568 kg/m$^3$. X-ray structural analysis shows that the product is crystalline.

The storage behavior of this sample was evaluated in a desiccator test. For this, a 3 g sample is stored in an open weighing cup in a desiccator at 20° C. and a relative atmospheric humidity of 76% over a period of 144 hours. The mass increase in the sample is then ascertained and the pourability of the sample is evaluated. The mass increase was 20.4% and the sample was only slightly caked and could be converted again to the pourable state by gentle tapping.

Working Example 3 (According to the Invention)

Agglomerating Spray-Drying in a Spray-Tower with Integrated Fluidized Bed (Fluidized Spray Dryer (FSD))

500 g of a 41% strength aqueous Na3-MGDA solution with a total solids content of 46% by weight was diluted with 150 g of deionized water. The solution was then stirred in a glass flask with stirrer at room temperature and then fed to a spray dryer with integrated fluidized bed on the laboratory scale, with introduction of drying air at 130° C., an inlet air temperature of the fluidized bed of 110° C. and atomized via a two-material nozzle. In the first phase of the drying process, the liquid droplets were dried, with formation of the granulation seeds in the bed. The bed temperature was then reduced in order to initiate the granulation phase, during which the granulation cores were agglomerated with feed solution. The resulting granules were removed continuously from the spray dryer. Granulation of the solution was carried out in a range for the bed temperature between 64° C. and 74° C. The product had a residual moisture of 6.5% by weight, a high bulk density of 700 kg/m$^3$ and was very readily pourable. After 144 hours in the desiccator at 20° C. and a relative humidity of 76%, the product remained pourable, the X-ray diffractogram (FIG. 3) indicated a crystalline fraction of 70%.

Working Example 4 (According to the Invention)

Spray-Granulation with the Addition of Crystalline Fine Dust

Aqueous Na3-MGDA solution with a solids content of 48.8% was spray-granulated on a continuously operated laboratory spray-fluidized-bed. The conical fluidized bed with a diameter at the bottom of 150 mm and at the top of 300 mm had internal hose filters and a pneumatic atomization nozzle, with which spraying was achieved into the fluidized bed from below. The fluidized bed was operated with 55 Nm$^3$/h of nitrogen, an inlet temperature of 140° C. and a fluidized-bed temperature of 79° C. Na3-MGDA spray granules from previous experiments were introduced as initial charge into the fluidized bed. Over a period of 1.92 hours, an amount of 6.03 kg of solution in total was sprayed in. For this, the pneumatic atomization nozzle was operated with 4.7 Nm$^3$/h of nitrogen at room temperature and at a pressure of 3.3 bar (absolute). Solid was discharged from the fluidized bed via a screw such that the level of the fluidized bed remained constant. The discharged solid was sieved out every 30 minutes. 46.8% of the discharged particles were in the particle size range from 355 to 1250 μm. The bulk density of this fraction was 778 kg/m$^3$ and its water content was 11.8 mass %. The sieved out fines fraction of less than 355 μm was returned to the fluidized bed every 30 minutes.

The product prepared in this way was flowable granules. X-ray structural analysis shows that the product comprises crystals of the first modification defined above and is 71% crystalline.

The storage behavior of this sample was evaluated in the desiccator test. For this, a 3 g sample is stored in an open weighing cup in the desiccator at 20° C. and a relative atmospheric humidity of 76% over a period of 144 hours. The mass increase of the sample is then ascertained and the pourability of the sample is evaluated. The mass increase was 25.8% and the sample was only slightly caked and could be converted again to the pourable state by gentle tapping.

The invention claimed is:

1. A process for preparing a powder comprising at least one methylglycine-N,N diacetic acid complexing agent salt of formula (I):

wherein
R' is

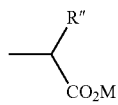

and
R" is methyl;
M is, independently, hydrogen, an alkali metal, an alkaline earth metal, ammonium or a substituted ammonium in corresponding stoichiometric amounts, provided that at least one M is not hydrogen;
comprising:
(a) atomizing an aqueous solution comprising a first complexing agent salt of formula (I) in the presence of a crystalline fine dust of a second complexing agent salt of formula (I), to produce a powder, and
(b) drying the powder,
wherein
a concentration of the first complexing agent salt in the aqueous solution is from 10 to 80% by weight, based on a total weight of the aqueous solution;
an upper limit for an average particle diameter of the crystalline fine dust is lower by at least a factor of 2 than a lower limit of an average particle diameter of the powder obtained by the process;
a fraction of the crystalline fine dust is from 0.1 to 20% by weight, based on a weight of the powder obtained in the process; and
the residual moisture of the powder after drying is 6.5 to 14% by weight.

2. The process of claim 1, wherein the drying occurs in a spray-tower.

3. The process of claim 1, wherein the drying is a spray-granulation in which, during the atomizing, the aqueous solution is sprayed into a fluidized bed comprising granules of the complexing agent salt of formula (I).

4. The process of claim 2, wherein, in the spray-tower, a fluidized bed is integrated and an agglomerating spray-drying occurs.

5. The process of claim 1, wherein the drying is a spray-agglomeration carried out in a mixer with agitated internals, to give an agglomerate which is then fully dried in a further apparatus.

6. The process of claim 1, wherein the aqueous solution comprises ca. 30 to 50% by weight of the complexing agent salt, and is concentrated in a process upstream of the spray-drying process in a heat exchanger or a thin-film evaporator to ca. 55 to 80% by weight of the complexing agent salt, based on the total weight of the aqueous solution.

7. The process of claim 1, wherein the drying occurs at a pressure in the range from 0.1 bar absolute to 10 bar absolute.

8. The process of claim 1, wherein a residence time of the drying is in a range from 10 seconds up to 1 h.

9. The process of claim 1, wherein the first complexing agent salt of formula (I) and the second complexing agent salt of formula (I) are the same.

10. The process of claim 1, wherein the first complexing agent salt of formula (I) and the second complexing agent salt of formula (I) are different.

11. The process of claim 9, wherein at least one M is an alkali metal.

12. The process of claim 11, wherein each M is an alkali metal, and each M is the same alkali metal.

13. The process of claim 12, wherein M is sodium and wherein the process produces a methylglycine-N,N-diacetic acid trisodium salt powder with a degree of crystallinity of ≥30% comprising a first crystalline modification with the d values stated below in Angströms at the diffraction angles 2-theta in °:

| 2-theta (°) | d value (Angströms) |
| --- | --- |
| 8.4 | 10.5 |
| 9.5 | 9.3 |
| 11.1 | 8.0 |
| 13.2 | 6.7 |
| 13.9 | 6.35 |
| 15.8 | 5.6 |
| 16.5 | 5.36 |
| 16.84 | 5.26 |
| 17.34 | 5.11 |
| 17.67 | 5.02 |
| 18.92 | 4.69 |
| 20.29 | 4.37 |
| 21.71 | 4.09 |
| 22.3 | 3.98 |
| 23.09 | 3.85 |
| 24.74 | 3.59 |
| 25.36 | 3.51 |
| 27.04 | 3.29 |
| 28.28 | 3.15 |
| 29.63 | 3.01 |
| 30.09 | 2.97 | and/or a second crystalline modification with the d values in Angstroms at the respective diffraction angles 2-theta in ° in the X-ray powder diffractogram corresponding to the table below:

| 2-theta (°) | d value (Angströms) |
| --- | --- |
| 8.2 | 10.80 |
| 10.5 | 8.40 |
| 15.55 | 5.70 |
| 16.47 | 5.38 |
| 17.09 | 5.18 |
| 18.10 | 4.90 |
| 18.82 | 4.71 |
| 21.00 | 4.23 |
| 21.35 | 4.16 |
| 22.64 | 3.92 |
| 23.69 | 3.75 |
| 24.73 | 3.60 |
| 26.75 | 3.33 |
| 28.93 | 3.08 |
| 29.88 | 2.99 |
| 31.46 | 2.84 |
| 31.88 | 2.80. |

14. The process of claim 1, wherein the process produces a methylglycine-N,N-diacetic acid trisodium salt powder with a degree of crystallinity of ≥70%.

15. The process of claim 1, wherein the process produces a methylglycine-N,N-diacetic acid trisodium salt powder that is crystalline.

* * * * *